United States Patent [19]

Cleare et al.

[11] Patent Number: 4,657,927
[45] Date of Patent: Apr. 14, 1987

[54] MALONATO PLATINUM COMPOUNDS

[75] Inventors: Michael J. Cleare; James D. Hoeschele; Barnett Rosenberg; Loretta Van Camp, all of East Lansing, Mich.

[73] Assignee: Research Corporation, New York, N.Y.

[21] Appl. No.: 497,806

[22] Filed: May 25, 1983

Related U.S. Application Data

[62] Division of Ser. No. 902,706, May 4, 1978, abandoned.

[51] Int. Cl.⁴ .............................................. A61K 31/28
[52] U.S. Cl. .................................................... 514/492
[58] Field of Search ......................... 424/287; 514/492

Primary Examiner—Jerome D. Goldberg
Attorney, Agent, or Firm—Scully, Scott, Murphy & Presser

[57] ABSTRACT

Malonato platinum coordination compounds and a method of treating malignant tumors sensitive to a planar $dsp^2$ platinum (II) coordination compound or an octahedral $d^2sp^3$ platinum (IV) coordination compound comprising the parenteral administration to an affected animal of a solution of the compound.

4 Claims, No Drawings

MALONATO PLATINUM COMPOUNDS

This is a Divisional, of Application Ser. No. 902,706, filed May 4, 1978, abandoned.

BACKGROUND OF THE INVENTION

The present invention relates to novel malonato platinum coordination compounds and to their use in cancer chemotherapy.

SUMMARY OF THE INVENTION

The invention provides platinum coordination compounds having the formula:

$$[Pt(II)A_x(OOC)_2-CRR_1]$$

or $$\text{cis or trans}[Pt(IV)A_x(OOC)_2-CRR_1)yL_z]$$

wherein:
- $x = 1$ or 2;
- $y = 1$ or 2;
- $z = 0$, 1 or 2, provided that when $y = 2$, $z = 0$ and when $y = 1$, $z$ is greater than 0;
- R and $R_1$ are selected from the group consisting of H, lower alkyl, aryl, aralkyl, alkenyl, cycloalkyl, cycloalkenyl, alkoxy, OH, or are combined with the carbon atom to form a cycloalkyl or cycloalkenyl group, and substituted derivatives thereof;
- when $x = 1$, A is $HR_2N-CHR_3-CHR_4-NR_5H$ and when $x = 2$, A is $H_2NR_6$ a heterocyclic amine or an amino acid, wherein $R_2$, $R_3$, $R_4$ and $R_5$ are the same or different and are selected from the group consisting of H, $CH_3$, $C_2H_5$, hydroxy and lower alkoxy provided that $R_2$ and $R_5$ may also be aryl or aralkyl, and each $R_5$ is the same or different and is selected from the group consisting of H, lower alkyl, aryl, aralkyl, hydroxy lower alkyl, hydroxyl and alkoxyl amines, alkoxylalkylamines wherein all of said alkyl groups are lower alkyls and heterocyclic substituents including said N as a ring member;
- when $z = 1$, L is a bidentate anionic ligand, and when $z = 2$, L is a monodentate anionic ligand.

The invention also relates to a composition and method for treating malignant tumors sensitive to a planar $dsp^2$ platinum(II) coordination compound or an octahedral $d^2sp^3$ platinum(IV) coordination compound in animals comprising parenterally administering to an animal affected with such a malignant tumor a solution containing a platinum coordination compound as defined hereinabove in an amount sufficient to cause regression of the tumor.

DETAILED DESCRIPTION OF THE INVENTION

Platinum coordination compounds and methods for their production are described by J. C. Bailar, Jr., *The Chemistry of the Coordination Compounds*, Reinhold Publishing Corp., N.Y., 1956, Chap. 2; J. Lewis et al, *Modern Coordination Chemistry: Principles and Methods*, Interscience Publishers, Inc., N.Y., 1960 and Kauffman *Inorganic Synthesis*, 7, McGraw-Hill Book Co., Inc., N.Y., 1963.

Platinum(II) forms $dsp^2$ coordination compounds which have a square planar arrangement in space. Platinum(IV) forms $d^2sp^3$ coordination compounds which have an octahedral arrangement in space.

The coordination compounds of the invention include the cis and trans isomers of platinum(II) and platinum(IV) which contain the bidentate malonato ligand which may be substituted or unsubstituted. The malonato ligand may contain substituents selected from the group consisting of lower alkyl, (e.g., methyl, ethyl, n-propyl, isopropyl, n-butyl, etc.); aryl, (e.g., phenyl; lower alkyl-, lower alkenyl-, halo-, nitro-, lower alkoxy-substituted phenyl and naphthyl); aralykyl, (e.g., phenylmethyl(benzyl), 2-(1-naphthyl)methyl); alkenyl, (e.g., 4-amino-1-butene, allyl); cycloalkyl, (e.g., cyclopropyl, cyclohexyl, etc.); cycloalkenyl, (e.g., 2-cyclopenten-1-yl, 2-cyclohexen-1-yl); alkoxy, (e.g., methoxy, ethoxy, etc.), and hydroxy. Also suitable are the 1,1-cycloalkylenedicarboxylic acids, (e.g., 1,1-cyclopropanedicarboxylic acid, 1,1-cyclobutanedicarboxylic acid, etc.) and the 1,1-cycloalkenyldicarboxylic acids, (e.g., 1,1-cyclopropenedicarboxylic acid, 1,1-cyclobutenedicarboxylic acid, etc.)

The coordination compounds of the invention also contain two monodentate ammonia or primary or heterocyclic amine ligands, i.e., when x in the above formula is 2 or one bidentate amine liquid, i.e., when x is 1.

Suitable monodentate amine ligands include lower alkyl amines, (e.g., methyl-, ethyl-, n-propyl-, isopropyl-, n-butyl-amines, etc.), aryl amines, (e.g., aniline), aralkyl amines, (e.g., benzylamine), hydroxy lower alkyl amines, (e.g., ethanolamine, propanolamine, etc), hydroxylamine, lower alkoxyl amines (e.g., methoxylamine, etc.), alkoxyalkylamines (e.g., methoxymethylamine, etc.), and heterocyclic amines (e.g., pyridine and aziridine). Also included are the amino acids, i.e., $R_7-CHNH_2-COOH$ wherein $R_7$ is H, lower alkyl (e.g., methyl, isopropyl, etc.), hydroxy lower alkyl (e.g., hydroxymethyl, hydroxyethyl, etc.), aralkyl (e.g., benzyl, etc.).

It is to be understood that the coordination compounds of the invention may include two identical or different monodentate ligands.

Suitable bidentate amine ligands include the substituted and unsubstituted primary and secondary ethylenediamines. One or both of the carbon atoms of the ethylenediamine may contain substituents such as lower alkyl (e.g., methyl, ethyl), hydroxyl, alkoxy (e.g., methoxy, ethoxy, etc). Secondary ethylenediamines wherein one or more of the amine groups contains substituents such as listed above for the carbon atoms of the primary amine and aryl (e.g., phenyl) and aralkyl (, e.g. benzyl) may also be utilized.

The Pt(II) coordination compounds specified herein do not exist as geometrical isomers; however, the Pt(IV) compounds exist as cis and trans isomers. It is to be further understood that the invention is inclusive of the cis and trans isomers.

The Pt(IV) coordination compounds may also contain two monodentate or one bidentate anionic ligand where only one malonato ligand is present, i.e., where $y = 1$ in the above formula.

Suitable monodentate anionic ligands include chloride, bromide, iodide, nitrite, hydroxide, nitrate, sulfamate, etc. Among the bidentate anionic ligands which may be present are oxalate, pyrophosphate, dithioxalate.

It is to be understood that the invention includes those coordination compounds containing mixed monodentate anionic ligands.

The preferred compounds are those wherein R and $R_1$ in the above formula are H, methyl or ethyl, i.e., malonatoplatinum, methylmalonatoplatinum and ethylmalonatoplatinum coordination compounds. The most preferred Pt(II) compounds are those malonatoplatinum(II) compounds of the above formula wherein $x=1$ and $R_2$, $R_3$, $R_4$ and $R_5$ are each H, i.e., malonatoethylenediamine platinum(II), methylmalonatoethylenediamineplatinum(II) and ethylmalonatoethylenediamineplatinum(II); and wherein $x=2$ and each $R_6$ is H, i.e., malonatodiammineplatinum(II), methylmalonatodiammmineplatinum(II) and ethylmalonatodiammineplatinum(II).

The preferred Pt(IV) compounds are those wherein $x=2$, each $R_6$ is H and $y=2$, i.e., bismalonato (or bismethylmalonato or bisethylmalonato) diammine platinum(IV).

The coordination compounds of the invention may be prepared by one of a variety of well-known methods. A general method of preparation of the Pt(II) coordination compounds is as follows: Starting compounds having the formula cis-[Pt a(Hal)$_2$] wherein Hal is I, Cl or Br and A is one bidentate or two monodentate amine ligands (prepared by the method of S. C. Dhara, Indian J. Chem., Vol. 8, p. 193 (1970)) are reacted with silver nitrate to form the diaquo complex. The latter is then reacted with the malonate ion to form the coordination compounds of the invention. This method is represented by the following reaction scheme:

cis-[Pt ACl$_2$]+2AgNO$_3$+2H$_2$O→cis-[Pt A(H$_2$O)$_2$](NO$_3$)$_2$+2AgCl cis-[Pt A(H$_2$O)$_2$](NO$_3$)$_2$+H$_2$C—(COO)$_2$→[Pt A(OOC)$_2$—CH$_2$]+2NO$_3^-$+2H$_2$O wherein A is one bidentate amine ligand or two monodentate amine ligands.

The following non-limiting examples are illustrative of the methods for preparing the compounds of the invention.

EXAMPLE 1

Malonatodiammineplatinum(II)

[Pt(NH$_3$)$_2$(C$_3$H$_2$O$_4$)]

Reactions:

[Pt(NH$_3$)$_2$Cl$_2$] + 2AgNO$_3$ + 2H$_2$O ⟶    I

[Pt(NH$_3$)$_2$(H$_2$O)$_2$](NO$_3$) + 2AgCl

[Pt(NH$_3$)$_2$(H$_2$O)$_2$](NO$_3$)$_2$ + C$_3$H$_2$O$_4^{2-}$ ⟶    II

[Pt(NH$_3$)$_2$(C$_3$H$_2$O$_4$)] + 2NO$_3^-$ + 2H$_2$O.

Silver nitrate (22.55 g—slightly less than the stoichiometric amount in order to avoid silver contamination) was dissolved in water (50 ml.) and added to [Pt(NH$_3$)$_2$Cl$_2$] (20 g) in a 250 ml conical flask. The contents were warmed (60° C.) on a hot plate with rapid stirring until the silver chloride precipitation was complete and the mother liquor was almost colorless. The silver chloride was filtered off using a fine pore sintered glass filter and the precipitate was washed several times with hot water to give a total filtrate volume of 100–200 ml.

Malonic acid (13 g—a twofold excess) was dissolved in water (30 ml) and neutralized with a solution of KOH (~13 g in 30 ml) to pH 5-6. The resulting potassium malonate solution was added to the platinum containing filtrate and the mixture was carefully warmed (to avoid "bumping") on the hot plate until white crystals of the product started to form in great quantity. The mixture was then cooled to room temperature and the product filtered off. The filtrate was reheated for 5-10 minutes and cooled to 0° C. to collect a further crop. The crude yield at this stage was 20.5 g (93%).

The product was recrystallized by dissolving in boiling or near boiling water. The above yield (20.5 g) required about 3 liters of boiling water for complete dissolution. Malonic acid 1 g/L was dissolved in the water to suppress any hydrolysis*. The filtered solution was cooled to 0° C. to give white fluffy needles (18.25 g—83%).

*U.V./via spectral and conductivity studies have shown that hydrolysis is negligible.

The crystals decompose between 185°–190°. The structure of the product was verified cia an i.r. spectrum. Solubility of the product is low in cold water, i.e., 20 mg/100 mls at 20° C. and
43 mg/100 mls at 37° C., but
higher in near boiling water (90°–100° C.) ~0.65 g/100 ml.

The empirical composition was verified by elemental analysis:

Malonatodiammineplatinum(II)[Pt(NH$_3$)$_2$(C$_3$H$_2$O$_4$)]
Calculated for C$_3$H$_8$N$_2$O$_4$Pt.C: 10.88; H: 2.43; N: 8.46: Pt 58.9. Found C: 10.67; H: 2.35; N: 8.54; Pt 58.7.

EXAMPLE 2

[Pt(en)(C$_4$H$_4$O$_4$)](en = H$_2$N(CH$_2$)$_2$NH$_2$; C$_4$H$_4$O$_4^{2-}$ = O$_2$CCH(CH$_3$)CO$_2^{2-}$)

Silver nitrate (3.64 g) was dissolved in 20 ml of water and added to [Pt(NH$_2$)$_2$(CH$_2$)$_2$CL$_2$] (3.5 g) suspended in water (30 ml) in a conical flask. The mixture was stirred on a warm hot plate for 5-10 minutes until all the yellow platinum complex had dissolved to give a yellow liquor plus a copious white silver chloride precipitate. The mixture was filtered through a fine pore filter and the precipitate washed twice with small volumes of hot water. The clear filtrate plus washings was added to an aqueous solution of methylmalonic acid (2 g in 20 mls) which had been adjusted to pH 5-6. The mixture was heated to about 80° C. for five minutes and then cooled to 0° C. The shiny white crystals which formed were filtered and washed with cold water and acetone (Yield 2.65 g). The mother liquor plus aqueous washings was reduced to about half its original volume (~30 mls) to yield a second crop on cooling to 0° C. (Yield 0.85 g). Total Crude yield was 3.50 gms (88%). The complex was recrystallized from a minimum volume of boiling water (around 250 mls) with filtration through a fine pore filter prior to cooling to 0° C. Yield of shiny white leaflets 2.96 g (74%).

Calculated for C$_6$H$_{12}$N$_2$O$_4$Pt: C: 19.41 H 3.26 N: 7.55. Found C: 19.11 H 3.61 N: 7.89.

A second crop (0.33 g—8%) was obtained by reducing the bulk of the mother liquor.

EXAMPLE 3 trans-]Pt IV(NH$_3$)$_2$(mal)$_2$]

Silver nitrate (5.45 g) was dissolved in water (30 ml) and added to trans [Pt(NH$_3$)$_2$Cl$_4$] (3 g) suspended in water (30 mls) containing concentrated nitric acid (3 ml). The contents were warmed on a hot plate (70°–80° C.) and stirred for at least one hour. The mixture was filtered through a fine pore sintered glass filter to remove the silver chloride. The precipitate was washed twice with a small volume of hot water. The clear filtrate plus washings was tested with a drop of b 1M KCl solutions to determine if excess silver chloride was present. (If the test is positive, sufficient KCl is added dropwise to the bulk solution until no silver chloride is precipitated.) The solution was refiltered and the filtrate reduced to 20–30 mls in volume and cooled to 0° C. to yield plate yellow crystals (presumably trans (Pt(NH$_3$)$_2$(NO$_3$)$_4$]). These were washed with a little cold water and then acetone (Yield 1.8 g). A portion of this yield (1 g) was dissolved in a minimum of hot water to which sodium nitrate (0.2 g) had been added. This solution was filtered into an aqueous solution of malonic acid (0.5 g—a slight excess) which had been adjusted to pH 5–6 with sodium hydroxide. White nucro-crystals of the complex quickly form on cooling. These were filtered off and washed with cold water and acetone. (Yield 0.7 g—30–40%).

Calculated for C$_6$H$_{10}$N$_2$O$_8$Pt C: 16.63 H 2.33 N: 6.47. Found C: 16.60 H 2.64 N: 6.80.

GENERAL STRUCTURE CONFORMATION

The malonate group is shown to be coordinated to the platinum by the observed change in the electronic spectra on going from the aquo to the malonate species. Thus, structures such as [Pt(NH$_3$)$_2$(H$_2$O)$_2$]$_2$(H$_2$C$_3$O$_4$)] are ruled out confirming the analytical data. Similarly, zero-time conductivity measurements support a neutral compound. The i.r. spectra show the presence of coordinated carboxyl groups (1600–1650 cm and 1400 cm$^{-1}$) with no CO$_2$H groups (which would show at 1700–1750 cm). Finally the carboxyl group vibrations are compatible with a chelated structure as compared to oxalate complexes of known structures.

The compounds of the invention were tested for antitumor activity, i.e., for sensitivity to a planar dsp$^2$ platinum(II) coordination compound or an octahedral d$^2$sp$^3$ platinum(IV) coordination compound using our standard screening tumor, solid sarcoma 180 tumor in female Swiss white mice, following standard protocols for this testing as set by the National Cancer Institute. (*Cancer Chemotherapy Rep.*, 25 (1962)).

For these tests an S 180 tumor taken from a sacrificed mouse was disected free of superfluous tissue and cut under sterile conditions into approximately 10 milligram size pieces. These tissue pieces were then implanted by trocar in the left axillary region, subcutaneously, in new mice. The mice were, on the average, approximately four weeks old and weighed 18–20 grams. Taking day 0 as the day of implant, the animals were sacrificed on day 10. The tumors were excised and weighed and the ratio of the weights of the tumors in mice in the treated animals to the control set of animals was obtained. This ratio, multiplied by 100, is given as the T/C ratio in Table I.

For the first set of tests the coordination compound was freshly dissolved in sterile distilled water and injected intraperitoneally on day 1 into each of the test mice. The volume of the injection was usually ½ ml. In some cases, in order to get an active dose into the animal where the chemical was not soluble in this amount of solvent, a fine dispersion was prepared of the dose needed for the test. Thus, some of our test results were obtained on animals where a slurry of the compound was injected. These are so noted in Table I below. In addition, for some of the compounds, there was injected about 1 ml of solution, either in one single injection, or in 2 injections given a few hours apart of ½ ml each. These injections were initially given in 4 different dose levels for each new compound with 6 mice in each dose level. The tests covered a dose range from a low ineffective dose, to an upper dose level which produced some deaths within the time period of the experiment. The results are set forth in Table I.

TABLE I

Tests of Antitumor Activity (for sensitivity to a planar dsp$^2$ platinum (II) coordination compound or an octahedral d$^2$sp$^3$ platinum (IV) coordination compound) of Malonato and Substituted Malonato Coordination Complexes of Platinum.
Tumor-Sarcoma 180  Animal-Female Swiss white mice
Single injections on days noted, intraperitoneally

| Coordination Complex | Day of Injection | Dose Level | T/C | No. of Deaths |
|---|---|---|---|---|
| Malonatodi-ammineplatinum (II) (slurry in H$_2$O) | 1 | 10 mg/kg | 76 | 0 |
| | | 15 mg/kg | 38 | 0 |
| | | 20 mg/kg | 64 | 0 |
| | | 25 mg/kg | 31 | 0 |
| | | 30 mg/kg | 7 | 1/6 |
| | | 40 mg/kg | — | 6/6 |
| | | 50 mg/kg | 1 | 5/6 |
| | | 60 mg/kg | — | 6/6 |
| (solution in H$_2$O) | Daily for days 1–10 | 4 mg/kg | 54 | 0 |
| | | 5 mg/kg | 56 | 0 |
| | | 6 mg/kg | 23 | 0 |
| | | 7 mg/kg | 12 | 0 |
| Methylmalonato-diammineplatinum (II) (Solution in H$_2$O) | 1 | 30 mg/kg | 39 | 0 |
| | | 40 mg/kg | 26 | 0 |
| | | 50 mg/kg | 35 | 0 |
| | | 60 mg/kg | 6 | 0 |
| | | 70 mg/kg | 124 | 3/6 |
| | | 80 mg/kg | — | 6/6 |
| malonatoethylene-diamineplatinum (II) | 1 | 60 | 80 | 0 |
| | | 80 | 138 | 0 |
| | | 100 | 85 | 0 |
| | | 120 | 50 | 0 |
| ethylmalonato-ethylenediamineplatinum (II) | 1 | 40 | 72 | 0 |
| | | 60 | 81 | 0 |
| | | 80 | 79 | 0 |
| | | 90 | 47 | 0 |
| | | 100 | 55 | 1 |
| | | 110 | 41 | 0 |
| | | 120 | 58 | 0 |
| malonato-1,2 propylenediamine-platinum (II) | 1 | 45 | 50 | 0 |
| | | 60 | 9 | 1 |
| | | 75 | 16 | 3 |
| | | 90 | — | 5 |
| malonato-1,3 propylenediamine-platinum (II) | 1 | 20 | 69 | 0 |
| | | 40 | 79 | 0 |
| | | 60 | 21 | 0 |
| | | 80 | 35 | 1 |
| methylmalonato-ethylenediamineplatinum (II) (solution in H$_2$O) | 1 | 30 mg/kg | 78 | 0 |
| | | 40 mg/kg | 80 | 0 |
| | | 50 mg/kg | 51 | 0 |
| | | 60 mg/kg | 26 | 0 |
| | | 70 mg/kg | 20 | 1 |
| | | 90 mg/kg | 4 | 1 |
| ethylmalonato-diammineplatinum (II) (solution in H$_2$O) | 1 | 30 mg/kg | 57 | 0 |
| | | 40 mg/kg | 43 | 0 |
| | | 50 mg/kg | 47 | 0 |
| | | 60 mg/kg | 39 | 0 |
| | | 70 mg/kg | 17 | 0 |
| | | 80 mg/kg | 16 | 0 |
| malonatoethylene-diamineplatinum (II) (solution in H$_2$O) | 1 | 10 mg/kg | 88 | 0 |
| | | 20 mg/kg | 58 | 0 |
| | | 40 mg/kg | 18 | 0 |
| | | 45 mg/kg | 49 | 0 |
| | | 50 mg/kg | 35 | 0 |
| | | 55 mg/kg | 38 | 0 |
| | | 60 mg/kg | 15 | 3/6 |
| | | 80 mg/kg | 24 | 3/6 |

TABLE I-continued

Tests of Antitumor Activity (for sensitivity to a planar dsp$^2$ platinum (II) coordination compound or an octahedral d$^2$sp$^3$ platinum (IV) coordination compound) of Malonato and Substituted Malonato Coordination Complexes of Platinum.
Tumor-Sarcoma 180   Animal-Female Swiss white mice
Single injections on days noted, intraperitoneally

| Coordination Complex | Day of Injection | Dose Level | T/C | No. of Deaths |
|---|---|---|---|---|
| 1,1-cyclobutanedicar- | 1 | 20 mg/kg | 71 | 0 |
| boxylate diammine- | | 40 mg/kg | 60 | 0 |
| platinum (II) | | 60 mg/kg | 38 | 0 |
| | | 80 mg/kg | 42 | 0 |
| | | 100 mg/kg | 69 | 0 |
| | | 120 mg/kg | 18 | 0 |
| | | 160 mg/kg | 62 | 4 |
| malonatobis | 1 | 80 mg/kg | 58 | 0 |
| (methylamine) platinum | | 100 mg/kg | 53 | 0 |
| (II) | | 120 mg/kg | 28 | 0 |
| | | 140 mg/kg | 25 | 0 |
| | | 160 mg/kg | 17 | 1 |
| | | 180 mg/kg | 19 | 1 |

In addition to the day 1 injections described above, in a number of case injections were delayed until day 8 of tumor growth. In these cases the tumor was usually at least larger than ½ gm, as estimated by palpation. The animals were then injected and observed for a period of approximately 60 days. Activity was measured by the number of animals whose tumors had regressed to the vanishing point, while still allowing the animal to survive for this time period. Such test results are described in TABLE II below.

TABLE II

Tests of Large Sarcoma 180 Regressions by Malonato Coordination Complexes of Platinum.
Tumor-Sarcoma 180   Animal-Female Swiss white mice
Single injections on Day 8 intraperitoneally in H$_2$O solutions

| Coordination Complex | Dose | Total Number of Regressions | Deaths |
|---|---|---|---|
| malonatodi- | 14 mg/kg | 2 | 4 |
| ammineplatinum (II) | 16 mg/kg | 3 | 3 |
| | 18 mg/kg | 4 | 2 |
| | 20 mg/kg | 5 | 1 |
| malonatoethylene- | 40 mg/kg | 3 | 3 |
| diamineplatinum (II) | 45 mg/kg | 1 | 5 |
| | 50 mg/kg | 2 | 4 |
| | 60 mg/kg | 3 | 3 |

The results described in Tables I and II indicate that the compounds of the invention are very potent antitumor agents against the S 180 tumor in Swiss white mice.

Confirmatory tests of antitumor activity against the Walker 256 Carcinosarcoma in rats, and the ADJ/P-C6A tumor in mice were conducted. The initial test results are shown in Table III and confirm the potent action of the compounds of the invention against these other tumor systems.

TABLE III

Confirmatory Tests of Antitumor Activity (for sensitivity to a planar dsp$^2$ platinum (II) coordination compound or an octahedral d$^2$sp$^3$ platinum (IV) coordination compound)

| Dose | % Inhibition | Deaths |
|---|---|---|
| Malonatodiammineplatinum (II) | | |
| Turmor: Walker 256 Carcinosarcoma - Animal - Rat | | |
| Single injection Day 1 in Oil, Intraperitoneally | | |
| 10 mg/kg | 100 | 0 |
| 20 mg/kg | 100 | 0 |
| 40 mg/kg | 100 | 0 |
| 80 mg/kg | — | 0 |
| Malonatoethylenediammineplatinum (II) | | |
| Tumor: Walker 256 Carcinosarcoma - Animal - Rat | | |
| Single injection Day 1 in Oil, Intraperitoneally | | |
| 10 | 1 | 0 |
| 20 | 25 | 0 |
| 40 | 100 | 0 |
| 80 | 100 | 0 |
| 160 | — | all |
| Tumor: ADJ/PC6A - Animal - Mouse | | |
| Single injection Day 25 in Oil, Intraperitoneally | | |
| 4 | 1.3 | 0 |
| 20 | 94 | 0 |
| 100 | 100 | 0 |
| 500 | — | all |

Samples of the malonato diammine and malonato ethylene diamine complexes of platinum(II) were submitted to the Drug Research and Development Branch of the National Cancer Institute for screening for antitumor activity against the L1210 tumor in mice. The results obtained on this tumor system are shown in Table IV. They confirm the activity of the compounds of the invention.

TABLE IV

Confirmatory Tests of Antitumor Activity (for sensitivity to a planar dsp$^2$ platinum (II) coordination compound or an octahedral d$^2$sp$^3$ platinum (IV) coordination compound) at the National Cancer Institute.
Tumor: L1210   Animal - Mice
Daily injections Days 1-9, Intraperitoneally

| Coordination Complex | Dose | % Increase in Lifespan |
|---|---|---|
| Malonatodi- | 50 mg/kg | 163 |
| ammineplatinum (II) | 25 mg/kg | 133 |
| | 12.5 mg/kg | 115 |
| Malonatoethylene- | 50 mg/kg | 101 |
| diammineplatinum (II) | 25 mg/kg | 160 |
| | 12.5 mg/kg | 151 |
| Malonatoethylene- | 37.5 mg/kg | 121 |
| diammineplatinum (II) | 25 mg/kg | 196 |
| (repeat test) | 16.5 mg/kg | 160 |
| | 11 mg/kg | 145 |

The malonatoplatinum coordination compounds of the invention are preferably dissolved or suspended in water or other pharmaceutically acceptable carrier liquids. The parenterally administerable composition should preferably contain from about 0.5 mg to about 10 mg per ml., it being understood that the amount may vary greatly depending upon the particular compound employed and the animal to be treated.

The platinum coordination compounds of the invention are preferably administered parenterally to an animal affected with a malignant tumor sensitive to a planar dsp$^2$ platinum(II) coordination compound or an octahedral d$^2$sp$^3$ platinum(IV) coordination compound. The duration of treatment and the dose level, of course, will depend in each case upon the size of the host animal, nature and size of the tumor, etc. Generally, however, a dose level of from about 20 to about 200 mg/kg of body weight per day will be sufficient. It is to be understood, however, that the platinum coordination compounds compounded with a suitable pharmaceutical carrier in the same proportions as recited above may also be administered orally at the same dosage levels.

We claim:

1. A method for treating malignant tumors sensitive to a planar $dsp^2$ platinum(II) coordination compound or an octahedral $d^2sp^3$ platinum(IV) coordination compound in animals which comprises parenterally administering to an animal affected with said malignant tumor a solution containing in an amount sufficient to cause regression of the tumor a platinum coordination compound of the formula:

$$[Pt(II)A_x(OOC)_2\text{---}CRR_1]$$

or $$\text{cis or trans } [Pt(IV)A_x((OOC)_2\text{---}CRR_1)_yL_z]$$

wherein:
x = 1 or 2;
y = 1 or 2;
z = 0, 1 or 2, provided that when y = 2, z = 0, and when y = 1, z is greater than 0;
R and $R_1$ are selected from the group consisting of H, lower alkyl, aryl, aralkyl, alkenyl, cycloalkyl, cycloalkenyl, alkoxy, OH and combine with the carbon atom to form a cycloalkyl or cycloalkenyl group;
when x = 1, A is $HR_2N\text{---}CHR_3\text{---}CHR_4\text{---}NR_5H$ and when x = 2, A is $H_2NR_6$ or an amino acid; wherein $R_2$, $R_3$, $R_4$ and $R_5$ are the same or different and are selected from the group consisting of H, $CH_3$, $C_2H_5$, hydroxy and lower alkoxy, provided that $R_2$ and $R_5$ may also be aryl or aralkyl and each $R_6$ is the same or different and is selected from the group consisting of H, lower alkyl, aryl, aralkyl, hydroxy lower alkyl, hydroxy- and alkoxyl-amines and alkoxyl alkyl amines;
when z = 1, L is a bidentate anionic ligand, and
when z = 2, L is a monodentate anionic ligand.

2. A method for treating malignant tumors sensitive to a planar $dsp^2$ platinum(II) coordination compound or an octahedral $d^2sp^3$ platinum(IV) coordination compound in animals which comprises orally administering to an animal affected with said malignant tumor a solution containing in an amount sufficient to cause regression of the tumor a platinum coordination compound of the formula:

$$[Pt(II)A_x(OOC)_2\text{---}CRR_1]$$

or $$\text{cis or trans } [Pt(IV)A_x((OOC)_2\text{---}CRR_1)_yL_z]$$

wherein:
x = 1 or 2;
y = 1 or 2;
z = 0, 1 or 2, provided that when y = 2, z = 0, and when y = 1, z is greater than 0;
R and $R_1$ are selected from the group consisting of H, lower alkyl, aryl, aralkyl, alkenyl, cycloalkyl, cycloalkenyl, alkoxy, OH and combine with the carbon atom to form a cycloalkyl or cycloalkenyl group;
when x = 1, A is $HR_2N\text{---}CHR_3\text{---}CHR_4\text{---}NR_5H$ and when x = 2, A is $H_2NR_6$ or an amino acid; wherein $R_2$, $R_3$, $R_4$ and $R_5$ are the same or different and are selected from the group consisting of H, $CH_3$, $C_2H_5$, hydroxy and lower alkoxy, provided that $R_2$ and $R_5$ may also be aryl or aralkyl and each $R_6$ is the same or different and is selected from the group consisting of H, lower alkyl, aryl, aralkyl, hydroxy lower alkyl, hydroxyl- and alkoxyl-amines and alkoxyl alkyl amines;
when z = 1, L is a bidentate anionic ligand, and
when z = 2, L is a monodentate anionic ligand.

3. A composition suitable for parenteral administration to an animal affected with a malignant tumor sensitive to a planar $dsp^2$ platinum(II) coordination compound or an octahedral $d^2sp^3$ platinum(IV) coordination compound comprising a pharmaceutically acceptable carrier and a platinum coordination compound of the formula:

$$[Pt(II)A_x(OOC)_2\text{---}CRR_1]$$

or $$\text{cis or trans } [Pt(IV)A_x((OOC)_2\text{---}CRR_1)_yL_z]$$

wherein:
x = 1 or 2;
y = 1 or 2;
z = 0, 1 or 2, provided that when y = 2, z = 0, and when y = 1, z is greater than 0;
R and $R_1$ are selected from the group consisting of H, lower alkyl, aryl, aralkyl, alkenyl, cycloalkyl, cycloalkenyl, alkoxy, OH and combine with the carbon atom to form a cycloalkyl or cycloalkenyl group;
when x = 1, A is $HR_2N\text{---}CHR_3\text{---}CHR_4\text{---}NR_5H$ and when x = 2, A is $H_2NR_6$ or an amino acid; wherein $R_2$, $R_3$, $R_4$ and $R_5$ are the same or different and are selected from the group consisting of H, $CH_3$, $C_2H_5$, hydroxy and lower alkoxy, provided that $R_2$ and $R_5$ may also be aryl or aralkyl and each $R_6$ is the same or different and is selected from the group consisting of H, lower alkyl, aryl, aralkyl, hydroxy lower alkyl, hydroxyl- and alkoxyl-amines and alkoxyl alkyl amines;
when z = 1, L is a bidentate anionic ligand, and
when z = 2, L is a monodentate anionic ligand, said compound being present in an amount sufficient to cause regression of said tumor.

4. A composition suitable for oral administration to an animal affected with a malignant tumor sensitive to a planar $dsp^2$ platinum(II) coordination compound or an octahedral $d^2sp^3$ platinum(IV) coordination compound comprising a pharmaceutically acceptable carrier and a platinum coordination compound of the formula:

$$[Pt(II)A_x(OOC)_2\text{---}CRR_1]$$

or $$\text{cis or trans } [Pt(IV)A_x((OOC)_2\text{---}CRR_1)_yL_z]$$

wherein:
x = 1 or 2;
y = 1 or 2;
z = 0, 1 or 2, provided that when y = 2, z = 0, and when y = 1, z is greater than 0;
R and $R_1$ are selected from the group consisting of H, lower alkyl, aryl, aralkyl, alkenyl, cycloalkyl, cycloalkenyl, alkoxy, OH and combine with the carbon atom to form a cycloalkyl or cycloalkenyl group;
when x = 1, A is $HR_2N\text{---}CHR_3\text{---}CHR_4\text{---}NR_5H$ and when x = 2, A is $H_2NR_6$ or an amino acid; wherein $R_2$, $R_3$, $R_4$ and $R_5$ are the same or different and are selected from the group consisting of H, $CH_3$, $C_2H_5$, hydroxy and lower alkoxy, provided that $R_2$ and $R_5$ may also be aryl or aralkyl and each $R_6$ is the same or different and is selected from the group consisting of H, lower alkyl, aryl, aralkyl, hydroxy lower alkyl, hydroxyl- and alkoxyl-amines and alkoxyl alkyl amines;

when $z=1$, L is a bidentate anionic ligand, and when $z=2$, L is a monodentate anionic ligand, said compound being present in an amount sufficient to cause regression of said tumor.

* * * * *

UNITED STATES PATENT AND TRADEMARK OFFICE
CERTIFICATE OF CORRECTION

PATENT NO.   : 4,657,927

DATED        : April 14, 1987

INVENTOR(S)  : Michael J. Cleare, et al.

It is certified that error appears in the above-identified patent and that said Letters Patent is hereby corrected as shown below:

On the title page, bracket 62: "Division of Ser. No. 902,706, May 4, 1978, abandoned." should read as --Division of Ser. No. 902,706, May 4, 1978, abandoned which is a divisional of U.S.S.N. 778,955 filed March 18, 1977 now Patent No. 4,140,707 which is a Continuation of U.S.S.N. 260,989 filed June 8, 1972 now abandoned.--

Signed and Sealed this

Seventh Day of March, 1989

*Attest:*

DONALD J. QUIGG

*Attesting Officer*  *Commissioner of Patents and Trademarks*

UNITED STATES PATENT AND TRADEMARK OFFICE
CERTIFICATE OF CORRECTION

PATENT NO. : 4,657,927            Page 1 of 3

DATED : April 14, 1987

INVENTOR(S) : Michael J. Cleare, et al.

It is certified that error appears in the above-identified patent and that said Letters Patent is hereby corrected as shown below:

Column 1, line 38: "$R_5$" should read as --$R_6$--

Column 2, line 25: "liquid" should read as --ligand--

Column 3, lines 11-12: "methylmalonato-diammminepltinum" should read as --methylmalonato-diamminepltinum--

Column 4, line 21: "185° - 190°" should read as --185° - 190°C--

Column 5, line 9: "b 1M KCl" should read as --1M KCl--

Column 5, line 37: "1600-1650 cm" should read as --1600-1650 $cm^{-1}$--

UNITED STATES PATENT AND TRADEMARK OFFICE
CERTIFICATE OF CORRECTION

PATENT NO. : 4,657,927

DATED : April 14, 1987

INVENTOR(S) : Michael J. Cleare, et al.

It is certified that error appears in the above-identified patent and that said Letters Patent is hereby corrected as shown below:

Column 9, line 23, Claim 1: "OH, and" should read as --OH, or--

Column 9, line 25, Claim 1: after "group;" insert --and substituted derivatives thereof--

Column 9, line 33, Claim 1: "hydroxy" should read as --hydroxyl--

Column 9, line 61, Claim 2: after "group;" insert --and substituted derivatives thereof--

Column 10, line 29, Claim 3: after "group;" insert --and substituted derivatives thereof--

Column 10, line 64, Claim 4: "OH, and" should read as --OH, or--

UNITED STATES PATENT AND TRADEMARK OFFICE
CERTIFICATE OF CORRECTION

PATENT NO. : 4,657,927

DATED : April 14, 1987

INVENTOR(S) : Michael J. Cleare, et al

It is certified that error appears in the above-identified patent and that said Letters Patent is hereby corrected as shown below:

Column 10 line 66, Claim 4: after "group;" insert

--and substituted derivatives thereof--

Signed and Sealed this

Eighth Day of May, 1990

Attest:

HARRY F. MANBECK, JR.

*Attesting Officer*    *Commissioner of Patents and Trademarks*